United States Patent [19]

Cole et al.

[11] Patent Number: 5,674,727
[45] Date of Patent: Oct. 7, 1997

[54] HUMAN CHORIONIC GONADOTROPIN BETA-SUBUNIT NICKING ENZYME

[76] Inventors: Laurence A. Cole, 402 Northwood Dr., Orange, Conn. 06477; Andrew Kardana, 225A Front St., New Haven, Conn. 06513

[21] Appl. No.: 298,189

[22] Filed: Aug. 31, 1994

[51] Int. Cl.$^6$ .................... C12N 9/50; C12N 9/48
[52] U.S. Cl. ........................ 435/219; 435/212
[58] Field of Search ........................ 435/212, 219

[56] References Cited

U.S. PATENT DOCUMENTS 5,252,489  10/1993  Macri ........................ 436/87

OTHER PUBLICATIONS

Nishimura et al. (1988) *Endocrinology*, 123(1), "Fragmentation of the β–Subunit of Human Chorionic Gonadotropin Produced by Choriocarcinoma", pp. 420–425.

Bidart et al. (1988) *Biochem. Biophys. Res. Comm.*, 154(2), "Characterization of a Cleavage Product in the Human Choriogonadotropin β–Subunit", pp. 626–632.

Puisieux et al. (1990) *Endocrinology*, 126(2), "Occurrence of Fragmentation of Free and Combined Forms of the β–Subunit of Human Chorionic Gonadotropin", pp. 687–694.

Birken et al. (1991) *Endocrinology*, 129(3), "The Heterogeneity of Human Chorionic Gonadotropin (hCG). II. Characteristics and Origins of Nicks in hCG Reference Standards", pp. 1551–1558.

Kardana et al. (1991) *Endocrinology*, 129(3), "The Heterogeneity of Human Chorionic Gonadotropin (hCG). I. Characterization of Peptide Heterogeneity in 13 Individual Preparations of hCG", pp. 1541–1550.

Cole et al. (1991a) *Yale J. Biol. Med.*, 64(6), "The Biological and Clinical Significance of Nicks in Human Chorionic Gonadotropin and Its Free β–Subunit", pp. 627–637.

Cole et al. (1991b) *Endocrinology*, 129(3), "The Heterogeneity of Human Chorionic Gonadotropin (hCG). III. The Occurrence and Biological and Immunological Activities of Nicked hCG", pp. 1559–1567.

Kardana et al. (1992) *Clin. Chem.*, 38(1), "Polypeptide Nicks Cause Erroneous Results in Assays of Human Chorionic Gonadotropin Free β–Subunit", pp. 26–33.

Kardana et al. (1994) *J. Clin., Endocrin. Metab.*, 79(3), "Human Chorionic Gonadotropin β–subunit Nicking Enzymes in Pregnancy and Cancer Patient Serum", pp. 761–767.

Kagimoto et al. (1995) *Biol. Pharm. Bull.*, 18(6), "Nicked Human Chorionic Gonadotropin (hCG) by a Thermolytic Endoprotease", pp. 810–817, in Scisearch 95:450780.

Kardana et al. (1996) *Oncol. Res.*, 8(1), "Gonadotropin β–Subunit Nicking Enzyme (GBNE), A Potential Marker of Early Malignancies", pp. 13–16, in BIOSIS 96:229699.

*Primary Examiner*—Jon P. Weber
*Attorney, Agent, or Firm*—Brian D. Voyce

[57] ABSTRACT

A substantially pure human chorionic gonadotropin beta subunit nicking enzyme (GBNE) has been purified from human blood serum. GBNE nicks the beta-subunit of human chorioinic gonadotropin at either Arg-44 or Gly-47, is an arginine specific metalloprotease, has an apparent molecular weight of between 150,000 and 430,000 daltons, and is partially inhibited by phenanthroline or leupeptin.

1 Claim, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 145 amino acids
        ( B ) TYPE: amino acid
        ( C ) STRANDEDNESS: Not Applicable
        ( D ) TOPOLOGY: Unknown ( i i ) MOLECULE TYPE: subunit of hormone, specifically the
        beta§ubunit of hCG ( i i i ) ORIGINAL SOURCE: human urine ( i v ) FEATURE:
        ( A ) NAME/KEY: beta subunit of hCG that is nicked by GBNE
        ( B ) LOCATION: hCG
        ( C ) IDENTIFICATION METHOD: N- terminal sequence analysis ( x ) PUBLICATION INFORMATION:
        ( A ) AUTHORS: Keutmann et alia
        ( B ) TITLE: "A Receptor-binding Region in Human
            Choriogonadotrophin/Lutoprin Beta S
        ( C ) JOURNAL: Proc Nat'l Acad Sci USA
        ( D ) VOLUME: 84
        ( E ) ISSUE: Not applicable
        ( F ) PAGES: 2038-2042
        ( G ) DATE: 1987

( x i ) SEQUENCE DESCRIPTION: SEQ ID NO:1:

```
Ser  Lys  Glu  Pro  Leu  Arg  Pro  Arg  Cys  Arg
 1                    5                         1 0

Pro  Ile  Asn  Ala  Thr  Leu  Ala  Val  Glu  Lys
                     1 5                        2 0

Glu  Gly  Cys  Pro  Val  Cys  Ile  Thr  Val  Asn
                     2 5                        3 0

Thr  Thr  Ile  Cys  Ala  Gly  Tyr  Cys  Pro  Thr
                     3 5                        4 0

Met  Thr  Arg  Val  Leu  Gln  Gly  Val  Leu  Pro
                     4 5                        5 0
```

| | | | | | | | | | |
|---|---|---|---|---|---|---|---|---|---|
| Ala | Leu | Pro | Gln | Val 55 | Val | Cys | Asn | Tyr | Arg 60 |
| Asp | Val | Arg | Phe | Glu 65 | Ser | Ile | Arg | Leu | Pro 70 |
| Gly | Cys | Pro | Arg | Gly 75 | Val | Asn | Pro | Val | Val 80 |
| Ser | Tyr | Ala | Val | Ala 85 | Leu | Ser | Cys | Gln | Cys 90 |
| Ala | Leu | Cys | Lys | Lys 95 | Ser | Thr | Thr | Asp | Cys 100 |
| Gly | Gly | Pro | Lys | Asp 105 | His | Pro | Leu | Thr | Cys 110 |
| Asp | Asp | Pro | Arg | Phe 115 | Gln | Asp | Ser | Ser | Ser 120 |
| Ser | Lys | Ala | Pro | Pro 125 | Pro | Ser | Leu | Pro | Ser 130 |
| Pro | Ser | Arg | Leu | Pro 135 | Gly | Pro | Ser | Asp | Thr 140 |
| Pro | Ile | Leu | Pro | Gln 145 | | | | | |

HUMAN CHORIONIC GONADOTROPIN BETA-SUBUNIT NICKING ENZYME

TECHNICAL FIELD

The present invention relates to novel methods for detecting reproductive cancers or their associated tumors and assay products for conducting such methods. A novel enzyme, has been found that has gonadotropin beta-subunit nicking activity. The presence of such an enzyme in a human fluid sample has been found to indicate the presence of a reproductive cancer or its associated tumor for both diagnostic or prognostic purposes.

BACKGROUND ART

Human chorionic gonadotropin (hCG) is a dimeric glycoprotein hormone composed of an alpha subunit containing 92 amino acids noncovalently joined to a beta subunit containing 145 amino acids. hCG is produced by placental tissue during pregnancy, and thus, has been used as a marker in specific binding assays for determining if a woman is pregnant. The alpha subunit of hCG has the same peptide structure as that of the pituitary hormones pituitary leutinizing hormone (LH), follicle-stimulating hormone, and thyroid-stimulating hormone. It is the beta subunit that distinguishes hCG from these other hormones.

Intact hCG has steroidogenic activity. However, in vivo, hCG can be dissociated into free alpha and beta subunits which have little or no biological activity. Also, hCG can be nicked so as to lose a peptide linkage either between amino acids 44 and 45 or between amino acids 47 and 48. Like the free subunits, nicked hCG has little or no biological activity, and may, in fact, be an antagonist of hormone action. The pathways that dissociate, nick, or degrade hCG are substantially unknown.

In order to study the hCG degradation pathways, immunoassays have been created to study intact hCG and intact beta subunit (less than 1% nicked molecules). Nicked hCG levels have been determined in the past by using a subtractive immunoassay, (Cole et al., 1991, Endocrinology, 129:1559–1567.)

Degradation products of hCG have been found to be useful as tumor markers. Free beta subunit has been found to be a tumor marker for testicular cancer, (Marcillac et al., 1992, Cancer Research, 52:3901–3907). In a study of 749 cancer samples, elevated free beta subunit levels, i.e. greater than 0.1 ng/ml were found in over 70% of samples from non-seminomatous testicular cancer and 50% of samples of seminomatous testicular cancer. The beta subunit core of hCG, the terminal degradation product of hCG, is also a tumor marker for gynecological cancers and is found in urine. Sometimes referred to as urinary gonadotropin peptides or fragment, this marker has been found to detect 82% of ovarian cancer, 59% of endometrial cancer, and 47% of cervical malignancies, (Cole et al., 1990, Gynecol. Oncol., 36:391–394).

SUMMARY OF THE INVENTION

A novel enzyme has been found that nicks the beta subunit of hCG or the beta subunit of LH. The gondaotropin beta-subunit nicking enzyme (GBNE) is an arginine-specific metalloprotease having an apparent molecular weight of between 150,000 and 430,000 daltons. GBNE can be found, in particular, in human blood serum and purified therefrom using conventional techniques known to those of ordinary skill in the art. GBNE nicks the beta hCG subunit both at the arginine residue at amine acid 44 in hCG and, to a lesser extent, at the glycine residue at amino acid 47. The nicking activity of GBNE is partially inhibited by phenanthroline, a known inhibitor of metalloproteases, or by leupeptin, a known inhibitor of proteases cleaving at arginyl residues.

While GBNE is normally found in the sera of pregnant women, it has also been discovered to be associated with the presence of tumors in both men and women. By using specific binding assays for either GBNE or the product of GBNE catalysis—nicked beta-hCG subunit, nickel hCG, nicked beta-LH subunit, or nicked LH—in human fluid samples, an important relationship has been uncovered linking the presence of GBNE in men and non-pregnant women to invasive cancers and their associated tumors. (For the purposes of this invention, "fluid samples" include serum, plasma, blood, ascites fluid, amniotic fluid, cerebral fluid, spinal fluid, saliva, or urine.)

In control samples of men and non-pregnant women having no known invasive cancers, GBNE activity was not evident in substantially all of the controls, even those with benign or inflammatory disease. However, in cases of patients having known reproductive cancers, including cervical, endometrial, ovarian, prostate, testicular, tubal, uterine, vaginal, and vulvar cancers or tumors, over 90% of the patients showed elevated GBNE levels. Thus, specific binding assays for determining the presence of GBNE are useful in the diagnosis or prognosis of reproductive cancers.

For the purposes of this invention, elevated enzyme levels indicative of GBNE activity in a fluid sample can refer to an amount of GBNE present in a fluid sample such that when an excess amount of intact gonadotropin substrate is added to the sample, equal to or greater than 10% of the intact added material is nicked. "Intact GBNE substrate" includes intact beta-hCG subunit, intact hCG, as well as intact beta-LH subunit, or intact LH. By "excess", an amount of intact GBNE substrate is referred to that is greater than the amount of GBNE believed to be present, for the substrate typically from 10 ng to 100 ug for a 0.2 ml serum sample. In formulating specific binding assays for GBNE or GBNE activity, one should keep in mind that GBNE is normally found in fluid samples in concentrations of between about 0.02 ng/ml in healthy non-pregnant women and men to about 20 ng/ml in persons with reproductive cancers in advanced stages.

The use of GBNE as a reproductive cancer marker can extend from a high-risk screening test for cancer, to screening in annual physicals, to the differential diagnosis of benign versus malignant cancers. It can also be used to follow therapy for the treatment of known reproductive cancers or associated tumors, giving prognostic indications.

PREFERRED EMBODIMENTS

In general, the present method for detecting reproductive cancers and associated tumors in humans comprises obtaining a fluid sample from a patient and using the sample in a assay that determines the presence or amount of a gonadotropin beta-subunit nicking enzyme (GBNE), wherein a level of greater than 10% GBNE activity is indicative of the presence of a reproductive cancer or its associated tumors.

GBNE Substrate Assays

A preferred means for detecting GBNE activity is to measure the presence of GBNE indirectly through a GBNE substrate assay. To do so, a predetermined amount of a GBNE substrate is added to a fluid sample. The mixture of substrate and fluid sample is incubated for a predetermined time and a predetermined temperature prior to assaying for the GBNE activity level. One of ordinary skill in the art could select a preferred temperature, realizing that, as in the kinetics of classic enzyme reactions, the higher the temperature, the shorter the time needed for incubation to produce the catalysis product. Thus, GBNE substrate assays can be run, for example, at 37° C. for fours hours or at 4° C. for 24 hours. Where the GBNE substrate assay determines the amount of nicked beta-hCG subunit, nicked hCG, nicked beta-LH subunit, or nicked LH, a result of greater than 10% of the added intact GBNE substrate being nicked after incubation indicates the presence of a reproductive cancer or associated tumor.

A preferred embodiment of a GBNE substrate assay is a scavenging specific binding assay. Such an assay comprises obtaining a human fluid sample to which is added an excess of intact GBNE substrate. The resulting mixture is allowed to incubate at a predetermined temperature for a predetermined time, according to the desire of the ordinarily skilled artisan. An excess of a first scavenging specific binding partner is added to the mixture, the scavenging specific binding partner being able to bind selectively to the intact GBNE substrate so as to form an intact GBNE substrate complex such as an intact beta-hCG subunit complex or an intact hCG complex. The scavenging specific binding partner is not able to bind to nicked GBNE substrate. ("Nicked GBNE substrate" includes nicked beta-hCG subunit, nicked hCG, nicked beta-LH subunit, or nicked LH.) The mixture is contacted with a second specific binding partner which is immobilized to an inert, non-fluid support, such as glass, plastics, or nitrocellulose. This second specific binding partner is able to bind to nicked GBNE substrate so as to form an immobilized nicked GBNE substrate such as immobilized nicked beta-hCG subunit complex or immobilized nicked hCG complex. The second specific binding partner is not able to bind to intact GBNE substrate complex.

The resulting immobilized GBNE substrate complex is contacted with a third labeled specific binding partner which is able to bind to the immobilized GBNE substrate complex. (For the purposes of this invention, "label" refers to all known conventional molecules used for measuring specific binding reactions, including radioisotopes, enzymes or enzyme substrates, or chemiluminescent, fluorescent, quenching, or absorbant compounds.) Unbound, labeled specific binding partner is removed or separated from the immobilized GBNE substrate complex such as by using a washing step. Finally, the presence or amount of labeled specific binding partner on the support is determined. From the amount of label present, one can calculate the level of GBNE activity and thus, the amount of GBNE that would be in the sample.

A specific binding assay kit for the above assay would comprise four elements. The first is an excess of intact beta-hCG subunit, intact hCG, intact beta-LH subunit, or intact LH with respect to the maximum amount of GBNE anticipated to be present in the sample. The second is an excess of the first scavenging specific binding partner with respect to the maximum amount of GBNE anticipated to be present in the sample. The third is the second specific binding partner immobilized to the inert, non-fluid support. The amount of second specific binding partner present on the support being sufficient to capture the maximum amount of nicked beta-hCG subunit, nicked hCG, nicked beta-LH subunit, or nicked LH produced by the addition and incubation. The final and fourth element is the third labeled specific binding partner, which again must be present in sufficient amounts to bind to the maximum amount of immobilized nicked complexes on the support. Examples of specific binding partners for the above assay or kit are known to those of ordinary skill in the art, and if not available either commercially of from research groups, can be raised in animals using conventional techniques.

An alternative preferred embodiment of the scavenging substrate assay is the subtractive substrate assay, which is actually comprised of two separate specific binding assays. The following subtractive substrate assay is described using intact beta-hCG subunit or intact hCG, but intact beta-LH subunit or intact LH can be substituted. A first specific binding assay is performed on a first aliquot of the sample. In this first specific binding assay, at least one specific binding partner to intact beta-hCG subunit or to intact hCG is used to determine the presence or amount of intact beta-hCG subunit or intact hCG. A known amount of excess intact beta-hCG subunit or intact hCG is added to the first aliquot of the sample. A second specific binding assay is performed on a second, equal aliquot of the sample. This second specific binding assay determines the presence or amount of total beta-hCG subunit or total hCG, wherein an identical known amount of excess intact beta-hCG subunit or intact hCG is added to the second aliquot of the sample. The amount of GBNE present in the sample is determined by calculating the presence or amount of nicked beta-hCG subunit or nicked hCG, i.e., the total beta-hCG subunit or total hCG determined from the second specific binding assay is subtracted from the intact beta-hCG subunit or intact hCG determined from the first specific binding assay. A level of greater than 10% GBNE activity is indicative of the presence of a reproductive cancer or its associated tumors.

A kit for the above subtractive substrate assay comprises two kits. The first is for the above first specific binding assay having at least one specific binding partner to intact beta-hCG subunit, intact hCG, intact beta-LH subunit, or intact LH so as to determine the presence or amount of intact GBNE substrate in a first aliquot of the sample, and having a known amount of excess intact GBNE substrate with respect to the maximum amount of GBNE anticipated to be present in the sample. The second kit is for the above second specific binding assay, having at least one specific binding partner to total beta-hCG, total hCG, total beta-LH subunit, or total LH so as to determine the presence or amount of total GBNE substrate in an identical second aliquot of the sample, and having an identical known amount of excess intact GBNE substrate as in the first kit. "Total GBNE substrate" includes total beta-hCG, total hCG, total beta-LH subunit, or total LH.

Another preferred embodiment of a substrate assay measures GBNE using an immobilized and labeled substrate which is able to be enzymatically cleaved by GBNE. Suitable substrates include intact GBNE substrates or a synthetic protein comprised of amino acids that form the active site for GBNE nicking in the beta subunit of hCG or LH. The making of such synthetic proteins would be known to those of ordinary skill in the art. For example, the beta-hCG subunit has the following amino acid sequence, starting at amino acid 34: Cys-Ala-Gly-Tyr-Cys-Pro-Thr-Met-Thr-Arg-Val-*Leu-Gln-Gly-*Val-Leu-Pro-Ala-Leu-Pro-Gln-Val-Val-Cys-Asn-Tyr-Arg-Asp (residues 34 to 61 of SEQUENCE ID NO:1). (*representing where the beta-hCG subunit is nicked. See Keutmann et al., 1987, Proc Natl Acad Sci U.S.A., 84:2038–2042.) The GBNE substrate can be immobilized through conventional techniques, including using a specific binding reaction or using bifunctional compounds. The label is attached to the substrate such that when GBNE cleaves the GBNE substrate, then the label is released from the substrate. A human fluid sample is contacted with the labeled substrate for a predetermined time so as to allow the substrate to be cleaved and label is released if GBNE is present in the sample. Any released label is separated from the immobilized substrate and one can determine either the presence or amount of labeled substrate, or the presence or amount of released and separated label. A specific binding assay kit for the above assay comprises the above labeled substrate immobilized to an inert, non-fluid support.

Direct GBNE Assays

A second preferred means of measuring GBNE and detecting reproductive cancers or associated tumors is to use specific binding assays that directly measure the presence of GBNE. Such means include immunometric or sandwich immunoassay formats and competitive assay formats.

A preferred embodiment of a sandwich format for the detection or measurement of GBNE comprises performing a sandwich specific binding assay with at least one immobilized specific binding partner for GBNE and at least one labeled specific binding partner for GBNE, and determining the presence or absence of GBNE from the detection of immobilized labeled specific binding partner. In one sandwich assay embodiment using a mobile labeled complex formation, a predetermined amount of a first labeled specific binding partner for GBNE is added to a fluid sample so as to form a labeled GBNE complex. An immobilized second specific binding partner is contacted with the labeled GBNE complex so as to allow the labeled GBNE complex to bind to the second binding partner which can bind to GBNE at a site different from that of the first specific binding partner. As in the substrate GBNE assays, the second specific binding partner is immobilized to an inert, non-fluid support. Any unbound first labeled specific binding partner is separated from the immobilized and labeled GBNE complex, and the presence or amount of immobilized and labeled GBNE complex in the fluid sample is determined. A specific binding assay kit for the above assay comprises a predetermined amount of the above first labeled specific binding partner for GBNE and the above second specific binding partner immobilized to an inert, non-fluid support.

In another sandwich assay format using immobilized labeled complex formation a first specific binding partner is immobilized to an inert, non-fluid support, the immobilized specific binding partner being able to bind to GBNE. A fluid sample is contacted with the immobilized first specific binding partner so as to form an immobilized GBNE complex. A predetermined amount of a second labeled specific binding partner is added to the immobilized GBNE complex. This second specific binding partner can bind to the immobilized GBNE complex so as to form a labeled and immobilized GBNE complex. Any unbound second labeled specific binding partner is separated from the immobilized and labeled GBNE complex, and the presence or amount of immobilized and labeled GBNE complex in the fluid sample is determined. A specific binding assay kit for the above assay comprises the above first specific binding partner immobilized to an inert, non-fluid support and a predetermined amount of the above second labeled specific binding partner.

A preferred embodiment of a competitive assay for the detection or measurement of GBNE comprises performing a competitive specific binding assay with at least one labeled specific binding partner for GBNE, and determining the presence or absence of GBNE from the detection of bound labeled specific binding partner. In particular, one adds a predetermined amount of a labeled GBNE conjugate to a fluid sample. Then, one immobilizes a first specific binding partner or an ancillary specific binding partner to an inert, non-fluid support. This first specific binding partner is able to bind to GBNE in the sample, labeled GBNE conjugate or an ancillary specific binding partner. The ancillary specific binding partner is able to bind to either a complex of the first specific binding partner and labeled conjugate or a complex of the first specific binding partner and GBNE.

The mixture of labeled GBNE conjugate and sample is contacted with either the immobilized first specific binding partner so as to allow the formation of immobilized and labeled GBNE complex or immobilized GBNE complex, or is contacted with the first specific binding partner and the immobilized ancillary specific binding partner so as to allow the formation of immobilized and labeled GBNE complex or immobilized GBNE complex. Any unbound labeled GBNE conjugate is separated from the immobilized and labeled GBNE complex or immobilized GBNE complex, and the presence or amount of immobilized and labeled GBNE complex in the fluid sample is determined. A kit for the above competitive assay comprises a predetermined amount of the above labeled conjugate and the above first specific binding partner immobilized on the support. In addition, the kit can have the above ancillary specific binding partner immobilized to the inert, non-fluid support instead of the first specific binding partner.

EXAMPLES

Serum Samples

For the assay described hereafter, blood samples were taken from a number of individuals. All samples were separated into serum within 1 hour and stored in a minus 20° C. freezer until tested.

For a study of the marker relationship between GBNE and reproductive cancers, GBNE activity levels were obtained using a subtractive substrate assay. A control group for testing the lack of GBNE consisted of 130 healthy non-pregnant persons. A first group of test samples were obtained from 57 persons with proven reproductive malignancy of surgically removed samples. A second group of test samples were obtained from 102 persons, having benign tumors and inflammatory disease.

GBNE activity was determined by using the scavenger immunoassay described above. In particular, a fluid sample is prepared using 0.2 ml of human serum from each individual. To the serum is added an aliquot of 25 ul of P8, a beta-hCG subunit standard solution having a concentration of 2 ug/ml. (P8 contains 6.4% (wt/wt) hCG and is from Yale University, New Haven, Conn., U.S.A.) This P8 aliquot provides 10 mg/L of beta-hCG subunits to the sample, more than sufficient to swamp existing sample beta-hCG levels which typically range from 0 to 0.22 mg/l. Other suitable standards include CR129 hCG or CR129 Beta-hCG subunit, both from Columbia University, New York, N.Y., U.S.A. The mixture of P8 and sample is incubated at 37° C. for at least 4 hours and up to 48 hours, preferably sixteen hours.

A 96 well microtiter plate was prepared. Each microtiter well had been previously coated with FTB11, a total free beta-hCG subunit monoclonal antibody from the Institute Gustave Roussy in Paris, France, using 200 ul per well of an ascites/antibody solution which is diluted 1:12,000 in an ammonium bicarbonate buffer at ph 9.5. Each plate was left overnight at 4° C. (One could have substituted the B204 antibody from Columbia University, New York, N.Y., U.S.A. for FTB11.) Prior to use in the assay, each well was washed three times with water.

To each well was added 0.1 ml of scavenger antibody 1E5 solution from an antibody concentration of 4 mg/L or 0.4 ug per sample. (1E5 is a free beta-hCG subunit monoclonal antibody obtained from the University of Alabama, Birmingham, Ala., U.S.A.) The function of 1E5 is to tie the binding site of intact P8 beta-hCG subunit molecules, leaving only nicked P8 beta-hCG subunits free to bind and be immobilized onto the well surface. The sample and P8 mixture was diluted by adding 1 ml of 0.1% BSA buffer. An aliquot of 0.1 ml of the diluted mixture was added to a well and incubated with the 1E5 solution for about two hours. After incubation, each well was washed three times with water.

For labelling the immobilized complexes, 200 ul of a peroxidase labeled antibody solution was added to each well. This solution comprised 109 ng/ml of BP502 in a 0.1M TRIS buffer containing 0.1% BSA, 3.7 g of calcium chloride, and no azides. (BP502 is a peroxidase labeled anti-beta hCG subunit polyclonal antibody from Bios Pacific, Emeryville, Calif., U.S.A.) The plates were shaken for about two hours at ambient temperature. After three washes with water to remove unbound BP502, 200 ul of a peroxidase substrate solution was added to each well. This solution was comprised of a 20 mg tablet of orthophenylenediamine/sodium perborate/phosphate/citrate buffer in 100 ml of water, available from Sigma Chemicals, St. Louis, Mo., U.S.A. The plates were shaken in the dark for 30 minutes at ambient temperature. To stop the peroxidase reaction, 50 ul of 4M HCl was added to each well. The absorbance of each well was read in a Flow Laboratories Titertek Multiscan NCC-340 plate reader, McLean, Va., U.S.A., set at 492 nm. The assay has cross reactivities with intact beta-hCG of about 6%. GBNE activity was expressed as a percentage of nicking of added P8.

The following were the results of the above scavenging assay on the samples:

TABLE 1

Correlation GBNE Activity to Cancer Diagnosis

| Group Identity | Group Size | Diagnosis | GBNE <10% | GBNE >10% |
|---|---|---|---|---|
| Control | 130 | Normal | 127 | 3 |
| Inflammatory | 102 | Benign | 97 | 5 |
| Cancer | 9 | Cervix | 0 | 9 |
| Cancer | 8 | Endometrial | 0 | 8 |
| Cancer | 19 | Ovary | 4 | 15 |
| Cancer | 10 | Prostate | 0 | 10 |
| Cancer | 5 | Testicular | 0 | 5 |
| Cancer | 4 | Uterine | 0 | 4 |
| Cancer | 2 | Vulva | 0 | 2 |

The raw data for Table 1 is presented in Table 2.

Clearly, TABLE 1 shows a strong correlation between GBNE activity measurements, that is the presence of GBNE in non-pregnant women and in men, and the presence of reproductive cancers and associated tumors in individuals having such activity. Assays determining the presence or amount of GBNE can be useful in the diagnosis or prognosis of reproductive cancer or their associated tumors in humans.

TABLE 2

Individual Serum Sample GBNE Activity Results

| Sample # | Diagnosis | % Nicking |
|---|---|---|
| 1 to 32 | Normal | 4 |
| 33 to 71 | Normal | 5 |
| 72 to 89 | Normal | 6 |
| 90 to 111 | Normal | 7 |
| 112 to 124 | Normal | 8 |
| 125 | Normal | 9 |
| 126 to 127 | Normal | 12 |
| 128 | Normal | 13 |
| 129 | Normal | 19 |
| 130 | Normal | 20 |
| 1 to 7 | Benign | 4 |
| 8 to 39 | Benign | 5 |
| 40 to 64 | Benign | 6 |
| 65 to 78 | Benign | 7 |
| 79 to 87 | Benign | 8 |
| 88 to 91 | Benign | 9 |
| 92 to 97 | Benign | 11 |
| 98 to 99 | Benign | 15 |
| 100 | Benign | 16 |
| 101 | Benign | 17 |
| 102 | Benign | 19 |
| 1 to 2 | Cervix | 25 |
| 3 | Cervix | 26 |
| 4 | Cervix | 27 |
| 5 | Cervix | 34 |
| 6 | Cervix | 42 |
| 7 | Cervix | 45 |
| 8 | Cervix | 62 |
| 9 | Cervix | 64 |
| 10 | Endometrium | 23 |
| 11 | Endometrium | 28 |
| 12 to 13 | Endometrium | 31 |
| 14 | Endometrium | 38 |
| 15 | Endometrium | 45 |
| 16 | Endometrium | 48 |
| 17 | Endometrium | 59 |
| 18 to 19 | Ovary | 7 |
| 20 to 21 | Ovary | 8 |
| 22 | Ovary | 16 |
| 23 to 25 | Ovary | 27 |
| 26 | Ovary | 33 |
| 27 to 28 | Ovary | 42 |
| 29 | Ovary | 43 |
| 30 | Ovary | 45 |
| 31 to 32 | Ovary | 46 |
| 33 | Ovary | 49 |
| 34 to 35 | Ovary | 54 |
| 36 | Ovary | 62 |
| 37 | Prostrate | 12 |
| 38 | Prostrate | 13 |
| 39 | Prostrate | 14 |
| 40 to 41 | Prostrate | 20 |
| 42 to 43 | Prostrate | 23 |
| 44 | Prostrate | 24 |
| 45 | Prostrate | 29 |
| 46 | Prostrate | 47 |
| 47 | Testis | 12 |
| 48 | Testis | 14 |
| 49 | Testis | 17 |
| 50 to 51 | Testis | 20 |
| 52 to 53 | Uterus | 19 |
| 54 to 55 | Uterus | 20 |
| 56 | Vulva | 29 |
| 57 | Vulva | 58 |

GBNE Enzyme

GBNE was purified from serum using the following method. Two ml of first trimester pregnancy serum was applied to the first of two 2.5 cm by 100 cm serially connected columns. The columns were filled with Sephacryl S200HR, gel filtration medium, equilibrated with 0.05 mol/L of ammonium bicarbonate. Serum was washed through the columns using 0.05 M/L sodium bicarbonate, and fractions were collected. Enzyme activity was detected in a peak eluted between 150,000 and 430,000 molecular weight markers.

The effect of protease inhibitors on GBNE was examined. The above scavenging assay was used adding P8 to a pool of serum samples from pregnant women. The following results show the GBNE activity levels and the effect of adding known inhibitors:

TABLE 3

Effect of Protease Inhibitors on GBNE

| Inhibitor added | Concentration | % Nicking |
|---|---|---|
| None | | 32 |
| Leupeptin | 0.035 mM | 26 |
| Leupeptin | 0.35 mM | 13 |
| Phenanthroline | 3.5 mM | 16 |
| Phenanthroline | 22 mM | 12 |
| Phenanthroline/Leupeptin | 22 mM/0.35 mM | 2 |

These results clearly show that GBNE is a metalloprotease, the inhibition by phenanthroline, and in particular, a metalloprotease that cleaves at the carboxyl side of arginyl residues, the inhibition by leupeptin.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

---

We claim:

1. A substantially pure, chorionic gonadotropin beta-subunit nicking enzyme, (GBNE), comprising an arginine-specific metalloprotease having an apparent molecular weight of between 150,000 and 430,000 daltons which is derived and purified from human blood serum, said GBNE being capable of nicking the beta subunit of human chorionic gonadotropin either at the arginine residue at amino acid 44 or the glycine residue at amino acid 47, wherein the nicking activity of said GBNE is partially inhibited by phenanthroline or by leupeptin.

* * * * *

UNITED STATES PATENT AND TRADEMARK OFFICE
CERTIFICATE OF CORRECTION

PATENT NO. : 5,674,727

DATED : 10/7/97

INVENTOR(S) : Laurence Cole, Andrew Kardana

It is certified that error appears in the above-identified patent and that said Letters Patent is hereby corrected as shown below:

Column 1, line 5, insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Twenty-ninth Day of June, 1999

Attest:

Q. TODD DICKINSON

*Attesting Officer*     *Acting Commissioner of Patents and Trademarks*